United States Patent [19]

Cronenwett et al.

[11] Patent Number: 4,505,265
[45] Date of Patent: Mar. 19, 1985

[54] REHABILITATION DEVICES

[76] Inventors: Anna E. Cronenwett, 443 Fourth St., Ann Arbor, Mich. 48103; Kathleen Doyle, 4836 Rivers Edge, Troy, Mich. 48098

[21] Appl. No.: 406,356

[22] Filed: Aug. 9, 1982

[51] Int. Cl.³ .................. A61B 19/00; A47C 13/00; A63H 33/04
[52] U.S. Cl. .................. 128/1 R; 297/133; 297/118; 272/113; 446/95; 446/901
[58] Field of Search .................. 297/DIG. 1, DIG. 6, 297/463, 443, 272, 258, 1-2, 118, 130, 133, 3; 46/DIG. 1, 201, 97, 24-26, 15; 128/80 A, 1 R; 272/113

[56] References Cited

U.S. PATENT DOCUMENTS

| | | | |
|---|---|---|---|
| 3,556,586 | 1/1971 | Beardmore | 297/DIG. 2 |
| 3,606,461 | 9/1971 | Moriyama | 297/118 |
| 3,730,522 | 5/1973 | Paczkowski | 272/113 |
| 3,780,469 | 12/1973 | Hancovsky | 272/113 |
| 3,911,512 | 10/1975 | Plate | 297/118 |
| 4,099,773 | 7/1978 | Chang | 297/258 |
| 4,129,296 | 12/1978 | Meyer | 297/272 |
| 4,129,960 | 12/1978 | Gale | 46/25 |
| 4,179,158 | 12/1979 | Flaum et al. | 297/118 |
| 4,205,876 | 6/1980 | Cetina | 297/118 |
| 4,242,967 | 1/1981 | McMullen et al. | 46/25 |

FOREIGN PATENT DOCUMENTS

| | | | |
|---|---|---|---|
| 2035811 | 6/1980 | United Kingdom | 272/113 |
| 2049756 | 12/1980 | United Kingdom | 46/24 |
| 2082925 | 3/1982 | United Kingdom | 46/25 |

OTHER PUBLICATIONS

Whitney Brothers Co. catalog; 1970, p. 2, Item #5, "Toddlers Rocking-Roller".

Primary Examiner—C. Fred Rosenbaum
Assistant Examiner—Gene B. Kartchner
Attorney, Agent, or Firm—Basile, Weintraub & Hanlon

[57] ABSTRACT

An article of manufacture useful as a rehabilitation device, toy, article of furniture or the like includes a medial or central body portion (10), a pair of opposed legs (16), (18) extending from the body portion (10). The side walls of the legs are curvilinear, as is the bottom wall (12) of the central body portion (10). Each side wall of the article is covered with a woven nylon fabric for ready detachability of items such as woven nylon fabric letters, straps, etc. The article includes recesses (24) and projections (28) for stacking of plural articles.

7 Claims, 6 Drawing Figures

REHABILITATION DEVICES

BACKGROUND OF THE INVENTION

I. Field of the Invention

The present invention pertains to rehabilitation devices. More particularly, the present invention pertains to stackable articles of manufacture which are employable as rehabilitation devices. Even more particularly, the present invention concerns certain stackable articles of manufacture which can be arrayed into various configurations as both articles of furniture, toys as well as rehabilitation devices.

II. Prior Art

The need for devices to assist persons having inadequate motor control is a never ending search. The art has constantly striven to devise means and methods for increasing muscle strength as well as to provide means and modes of entertainment while accomplishing muscle strengthening. Heretofore, the art has considered systems of weights and pulleys, as well as braces and othe means of support.

The present invention, as will subsequently be detailed, provides nestable and stackable interrelated articles which can be arrayed as both articles of furniture, toys as well as rehabilitation devices.

The present invention is formed and arrayed from relatively inexpensive materials of construction which are easily deployed.

SUMMARY OF THE INVENTION

In accordance with the present invention there is provided a rehabilitation device derived from certain stackable articles of manufacture, including a base or basic unit. The basic unit hereof comprises an irregularly geometrically configured article having a medial or central portion or section and opposed, arcuate legs extending therefrom. The central body portion has an arcuate side wall which interconnects with the two opposed arcuate legs. The central portion has a length less than that of the two extending legs such that the overall appearance of the basic article is that of a "U" wherein the bottom wall or bight section of the "U" is concave, as opposed to the conventional convex.

The upper surface of the article proximate the outer terminus of each leg has a recess formed therein at each corner thereof. Each recess receives a projection formed on an analogous or complementary article to permit the stacking of plural articles.

In accordance herewith the exterior walls of an article are covered with a woven nylon fabric, i.e. Velcro. The Velcro is adhered to the walls by any suitable mode such as adhesives or the like.

By wrapping the article with items such as fabric straps, trays, containers, and other devices can be adhered thereto to facilitate utilization of the device.

The present invention further contemplates auxiliary articles such as a sinusoidally configured member having rollers associated therewith. By stacking or mounting one of the basic articles hereof thereonto a motive toy is thereby provided. Other auxiliary articles which use the basic article as an integral component are, also, devised.

In another embodiment hereof the basic article has a medial ledge incorporated thereinto whereby the instant article provides a foot recess when supporting a standing therapeutic position.

For a more complete understanding of the present invention reference is made to the following detailed description and accompanying drawing. In the accompanying drawing like reference characters refer to like parts throughout the several views in which:

DESCRIPTION OF THE PREFERRED EMBODIMENTS

Figure 1:
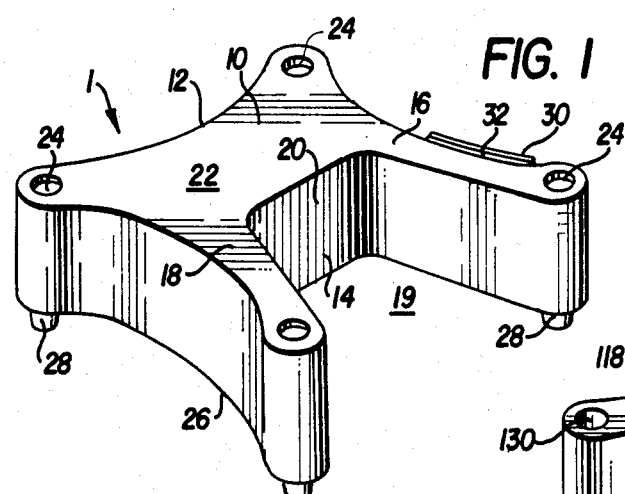
FIG. 1 is a perspective view of an article of manufacture usable as a rehabilitation device in accordance with the present invention.

Now, and with reference to the drawing, and in particular FIG. 1, there is depicted therein an article of manufacture which defines a rehabilitation device in accordance with the present invention. The article or rehabilitation device 1 hereof, generally, comprises a central body portion 10 having an upper wall 12 and an arcuate bottom wall 14. Laterally extending legs 16, 18 are integrally formed with and extend from the central portion 10. The legs extend overhead from the bottom wall 14 of the central section, as shown. In this manner a central recessed area 19 is defined between the opposed innerfaces of the legs 16, 18.

As shown in FIG. 1 each of the legs has an arcuate configuration and is disposed in an opposed manner to each other. The overall effect of the arcuate bottom wall 14 and the arcuate legs 16, 18 is to provide an article of manufacture having an irregular geometric pattern which simulates a "U" wherein the bight portion of the "U" is convex, as opposed to the conventional concave.

As shown in FIG. 1 the upper surface 22 of the article has a plurality of recesses 24 formed therein. The recesses are formed at the corners or apices or extremities of each of the legs.

The bottom wall 26 has a plurality of projections 28 projecting outwardly therefrom. The projections are axially aligned with the recesses and are positioned at the same point, but only on the bottom wall. In this manner a plurality of articles can be arrayed and stacked one atop the other with projections of one such article nesting or fitting in the recesses of an associated other article.

It should be noted with respect hereto that the articles need not be stacked in "overlying" coincidence or in symmetrical relationships. Rather, one article can be oriented in a manner shown that FIG. 1 and an associated article can be stacked thereupon which has been rotated 90, 180 or 270 degrees in a horizontal plane with respect to that shown in FIG. 1.

The side walls of the article, including the exterior or outer walls of the opposed legs as well as the interior walls thereof, the top wall 12 and the bottom wall 14 are covered with a woven nylon fabric 30, such fabric commonly being referred to as "Velcro". The fabric is adhered to the exterior walls by any suitable mode, such as gluing, adhesives, or the like. The fabric 30, as will subsequently be detailed, enables the article to be used in both a therapeutic manner as well as an educational device, furniture system, or as a toy.

Opptionally, intermediate the Velcro fabric 30 and the walls is disposed a padding 32 of any suitable material, such as foam cushion or the like. Where used, the padding is adhered to the side walls and, thereafter, the Velcro fabric 30 is adhered to the padding 32.

Where used as a therapeutic device a person having no muscle control can be stood against the walls through the use of body enveloping straps (not shown) having like nylon fabric portions associated therewith which adhere to the Velcro fabric walls of the article in the well-known manner. Likewise, the upper torso of a person can be maintained in an erect position by nesting the person within the recess 19 and being strapped thereto in the manner hereinabove described.

Figure 2:
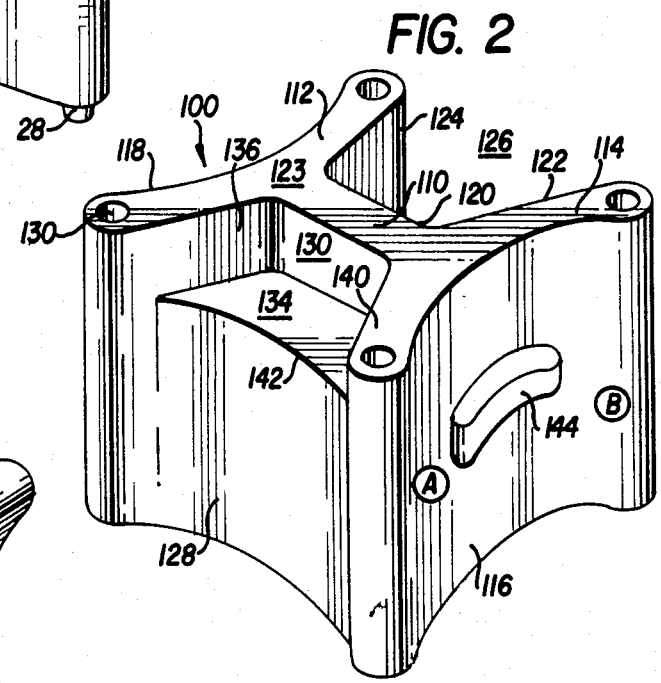
FIG. 2 is a perspective view of an alternate embodiment of the rehabilitation device of the present invention.

Referring now to FIG. 2 there is depicted therein an alternate embodiment of the article of the present invention, generally, depicted at 100. In accordance herewith the second embodiment, which defines a base for assembling a therapeutic or rehabilitation system, includes a central body section 110 having opposed legs 112, 114, respectively. The legs 112, 114 are integrally formed with and project above the central body portion 110, as shown. The legs are curvilinear on the exterior or outer perimeters thereof and thereby define opposed, curvilinear legs having walls 116, 118 defined thereby. The legs 112, 114, as noted, project above the top wall 120 of the central body portion 110. In this manner there is defined opposed interior leg walls 122, 124. The interior leg walls and the top wall 120 cooperate to define a recess 126 in the space defined therebetween.

The central body portion includes a bottom wall 128 which is, also, curvilinear in geometric configuration.

The article has an upper surface and a bottom surface (not shown). At each terminus of the legs on the upper surface of the article is provided a Velcro spot 130. The spots are used to detachably mount the article to a Velcro mat (not shown). By mounting the article onto a mat, during thereby, the article is kept stationary.

On the bottom wall of the article and at each terminus of each leg is a recess 132. The recesses function in the manner heretofore described and, therefore, for purposes of clarity such function will not be repeated herein.

The central body portion of the article 100 has a cutout portion or recess 134. The recess has side walls 136, 138, 140, as well as a bottom wall 142. The bottom wall 142 defines a cavity or recess into which a users feet can be inserted such that the front of the user's body can abut against the wall 128, for therapeutic purposes. Hence, the difference between this embodiment and that of FIG. 1 is the provision of the foot recess area by virtue of the cutout portion 134. In all other respects, except for size, and as noted above, this emobodiment is similar to that shown in FIG. 1.

FIG. 2 also depicts the utilization and deployment of the instant article of manufacture as an educational device. In accordance herewith and as shown in FIG. 2 a container 144 can be removably mounted onto the fabric by adhering a similar strip of fabric to the container 144. It is contemplated that Velcro letters, numbers or similar symbols be removably emplaced within the container. In this manner a user can merely select desired indicia from the container 144 and place them upon the side walls.

Figure 5:
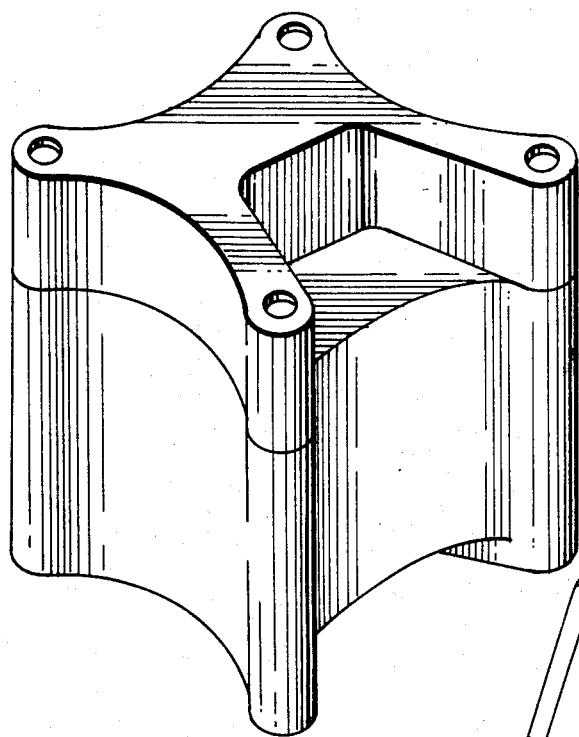
FIG. 5 is a perspective view showing a chair assembly derived from the articles hereof.

It should also be noted with respect hereto that in stacking or arraying, a combination of the articles of FIG. 1 and FIG. 2 can be employed. For example, and as shown in FIG. 5, a chain or seating system is assembled from the articles of FIG. 1 and FIG. 2 by stacking in the manner shown.

Figure 3:
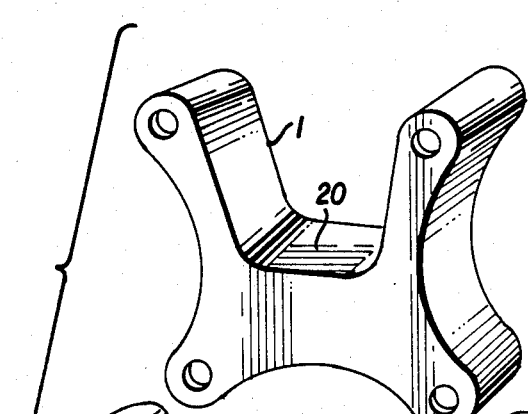
FIG. 3 is an exploded side elevational view of a toy constructed from the article of the present invention.

Referring now to FIG. 3 there is depicted therein the deployment of the instant article in a toy configuration. According to FIG. 3 there is provided a motive toy comprising separable members of a base, generally, denoted at 200 and the article 1.

The base 200 comprises a curvilinear member having a bottom wall 210 and a top wall 212. The base has a curvilinear configuration complementary to that of the bottom wall 12 of the article 1. Velcro strips 214 are adhered to the top wall 212 to permit removable mounting of the article 1 to the top wall 212. A ground engaging roller 216 (only one of which is shown) is rotatably mounted onto the base of each extremity thereof. To this end, each of the base 200 has a hollowed out portion 218. By hollowing out each extremity there is space created between the side walls 220, 222 of the base at each end thereof. An opening 224 is formed in each side wall proximate the end thereof. A pair of openings or holes 224 are associated with each other and in communication at the ends of the side walls, as shown. The openings serve to mount or journal an axle thereinto for rotatably mounting the roller 216. The axle can comprise a projection extending out of each lateral end of the roller, per se, or can comprise a spindle or other suitable member for rotatably mounting the roller through the openings or holes.

To employ the embodiment of FIG. 3 as a motive toy, the article 1 is mounted onto the top wall 212 as hereinabove indicated. A user then sits upon the top wall 20 of the article with the user's legs straddling between the upper wall and bottom wall. The user then engages the ground to push the toy in the direction desired, with the rollers facilitating movement thereof.

Figure 4:
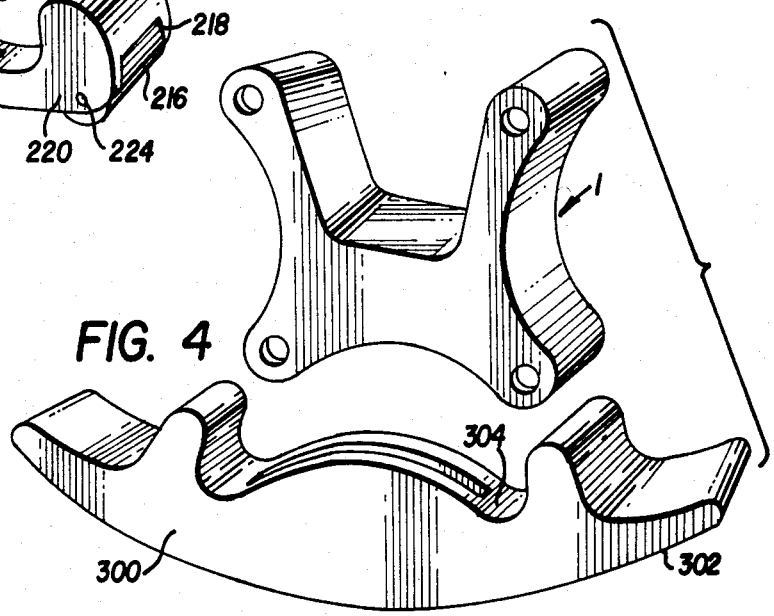
FIG. 4 is an exploded, side elevational view of another toy constructed from the article of the present invention.

Referring now to FIG. 4 there is depicted another toy employing the article 1 hereof. According to this embodiment the toy is a "rocker" having a ground-engaging base 300 having a bottom wall 302 which is convex in configuration. The article 1 is mounted onto the upper wall 304 of the base 300 in the same manner described with respect to the toy of FIG. 3. The user, again, straddles the sides of the device and merely rocks back and forth. Again, the article is detachably and separably mounted onto the base 300.

It is to be appreciated that various other configured bases can be conceived and separable toys defined thereby employing the article 1 hereof.

Figure 6:
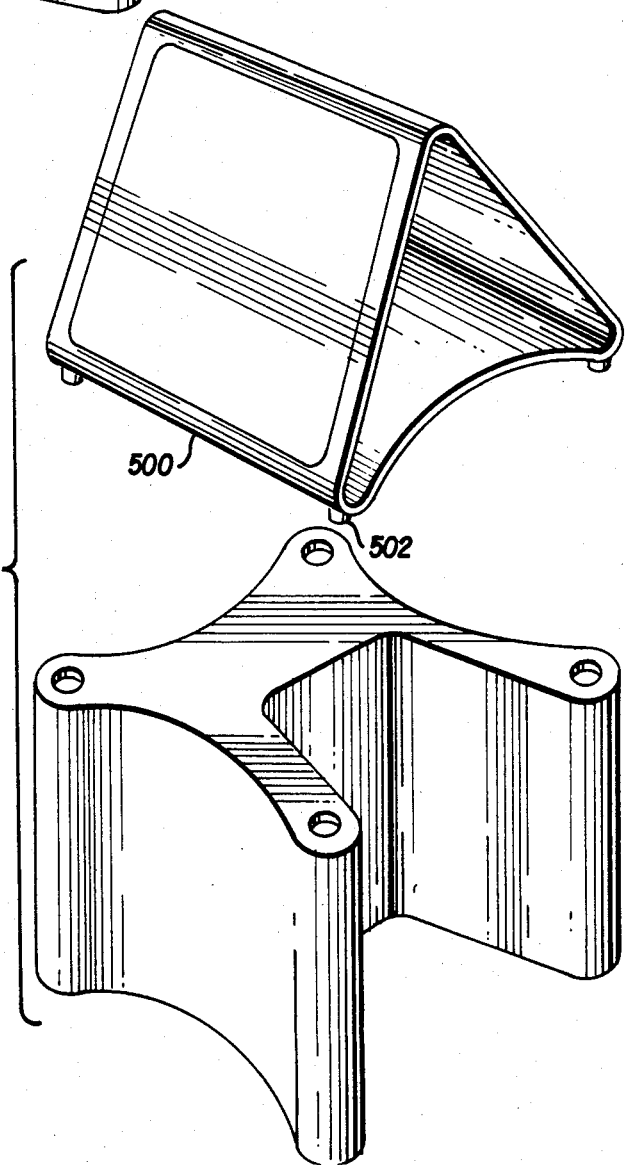
FIG. 6 is an exploded, perspective view of a combined easel board and article in accordance herewith.

Likewise, auxiliary items can be asssociated with the basic articles to enhance the utility thereof. For example, and as shown in FIG. 6, an easel board is detachably mounted to the article via stacking through projections 500 which fit into the recesses. The easel may have a Velcro surface 502, or other accoutrements. Likewise, table tops and other devices can be employed.

It should be noted with respect to the present invention that as a therapeutic device the configuration of the article evidences wide utility. It is to be appreciated that the organic or irregular geometric configuration is derived from a rectangle or square. However, it can be rotated into a variety of configurations for various therapeutic positions. Furthermore, the stacking permits of various heights to accommodate different size users. When used as a rehabilitation device the article supplies support to the knee, hip and chest when the user is in a standing position. Of course, this assumes the use of the support straps. When the user is placed in a kneeling position the article enables support of the hip and chest. Likewise, when a user is in a sitting position there is provided back support. Because of the strength of the support given the user can have its knees held out straight or in an abduction position depending on the mode in which the user is placed.

In manufacturing the instant article is can be formed from a durable light-weight material such as a foamed polystyrene, polyethylene, polycarbonate, polyurthane or similar foams having a "skin" exterior. Likewise, other light-weight materials can be used.

It is to be appreciated that there has been described herein an article of manufacture which can be arrayed and employed either as a therapeutic device in with various straps or as a toy depending on its orientation and through the configuration of a suitably designed base.

Having, thus, described the invention what is claimed is:

1. An article of manufacture for deployment as a rehabilitation device comprising:
   (a) a unitary central body portion having a top wall and a bottom wall, the bottom wall having a concave configuration,
   (b) a pair of opposed legs integrally formed with the central body portion, the legs extending from the bottom wall and projecting above the top wall of the central body portion, each leg having an exterior side wall and an interior side wall, each interior side wall extending from the top wall of the central body portion to a junction with an associated exterior side wall,
   (c) each exterior side wall of the legs and the bottom wall having a concave configuration, and
   (d) fabric fastener means adhered to at least certain portions of the bottom wall, the top wall and each side wall of the legs and cooperatable with a complementary fastener means for fastening the article to another object.

2. The article of claim 1 which further comprises:
   (a) at least one projection extending outwardly from one leg, the projection being disposed on one surface of the leg near a terminus thereof, and
   (b) at least one recess formed in one leg on a surface thereof opposite to that on which the projection is located, and wherein the projection and recess permit interlocking stacking of a plurality of suitably adapted articles.

3. The article of claim 1 which further comprises:
   a padding adhered to the top wall, the bottom wall and each side wall, the woven fabric being attached to the padding.

4. The article of claim 1 wherein:
   the central body portion has a cut-out section, the cut-out section having opposed side walls, an intermediate wall interconnecting the side walls, and a ledge extending from the bottom wall toward the top wall in a plane normal thereto, the ledge defining a cavity for insertion of a user's feet.

5. The article of claim 1 further comprising:
   (a) a base member having a bottom wall, and a curvilinear top wall,
   (b) a woven nylon fabric strip adhered to the top wall,
   (c) the article being removably mounted onto the top wall of the base member, and wherein the top wall of the base member has a curve complementary to that of the bottom wall of the article to enable the base member top wall and article bottom wall to contiguous mate along their respective arcs when the article is mounted onto the base.

6. The toy of claim 5 which further comprises:
   (a) a ground engaging roller disposed at each end of the base member.

7. The toy of claim 5 wherein:
   (a) the bottom wall of the base member is arcuate to enable it to rock back and forth on a ground surface.

* * * * *